United States Patent [19]

Shea, Jr.

[11] Patent Number: 4,862,881

[45] Date of Patent: Sep. 5, 1989

[54] ORTHOPAEDIC APPLIANCE

[76] Inventor: Cyril E. Shea, Jr., 61 Harwich Rd., West Springfield, Mass. 01089

[21] Appl. No.: 209,195

[22] Filed: Jun. 20, 1988

[51] Int. Cl.$^4$ .............................................. A61F 5/04
[52] U.S. Cl. ............................ 128/92 V; 128/92 VW
[58] Field of Search ............ 128/92 V, 303 B, 329 R, 128/92 VW, 92 VQ, 92 YE, 92 VY, 92 VD, 92 Z, 92 ZW, 92 YE, 92 VZ, 92 VV

[56] References Cited

U.S. PATENT DOCUMENTS

| 2,251,209 | 7/1941 | Stader | 128/92 YE |
|---|---|---|---|
| 2,388,482 | 11/1945 | Haynes | 128/92 YE |
| 4,421,112 | 12/1983 | Mains | 128/92 VY |
| 4,559,936 | 12/1985 | Hill | 128/92 VY |
| 4,566,448 | 1/1986 | Rohr | 128/92 VY |
| 4,567,886 | 2/1986 | Petersen | 128/92 VW |
| 4,613,324 | 9/1986 | Ghajar | 128/303 B |
| 4,627,425 | 12/1986 | Reese | 128/92 VY |
| 4,646,729 | 3/1987 | Kenna | 128/92 VW |
| 4,719,907 | 1/1988 | Banko | 128/92 V |

Primary Examiner—Edgar S. Burr
Assistant Examiner—Huong Q. Pham
Attorney, Agent, or Firm—Fishman, Dionne & Cantor

[57] ABSTRACT

This invention relates to an accessory orthopaedic appliance for use in arthroscopic surgery of the knee. The appliance is employed by attaching it to the patella in order to provide a means for holding and shifting the patella in any direction necessary to achieve optimal visualization of the undersurface of the patella.

5 Claims, 3 Drawing Sheets

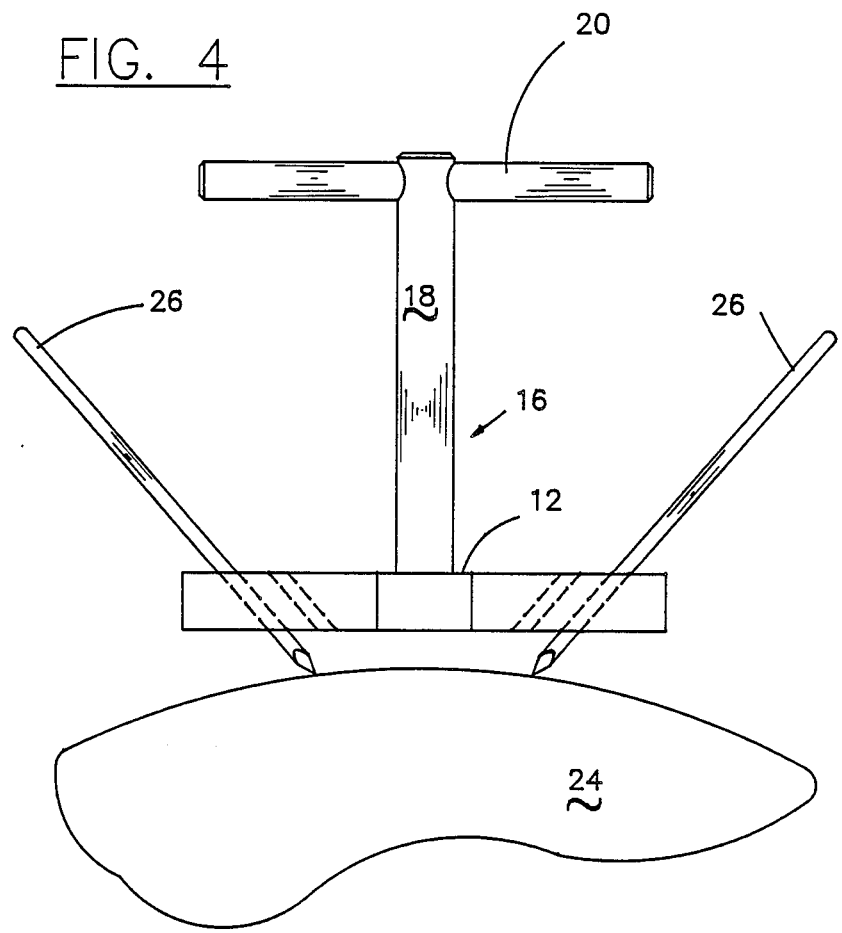

ORTHOPAEDIC APPLIANCE

BACKGROUND OF THE INVENTION

This invention relates to an orthopaedic appliance. In particular it relates to an orthopaedic appliance which is used as an accessory in arthroscopic surgery of the knee.

The patella or kneecap is essentially a thick flat triangular shaped moveable bone that forms the anterior point of the knee and protects the front of the knee joint.

In arthroscopic surgery of the knee, it is often necessary to view the undersurface of the kneecap. In order to achieve optimal visualization, the kneecap must shifted from position to position and held in place. While this may be accomplished by the arthroscopic surgeon with his hands in direct contact with the kneecap, said manipulation is often times less than desirable in that the kneecap may be difficult to grasp and move with one hand.

It is an object of the present invention to provide a device which may be attached to a person's kneecap so as to permit controlled movement thereof.

It is another object of the present invention to provide a device which may be attached to a person's kneecap by the use of a plurality of pins.

It is a further object of the present invention to provide an orthopaedic applicance which is easily constructed out of stainless surgical steel or other suitable material.

It is a further object of the present invention to provide a device which may be attached to a person's kneecap and held in position without relative movement between the kneecap and the device during manipulation of the kneecap during arthroscopic surgery.

The above and other objects of the present invention will become more apparent when considered in view of the following description and the drawings, in which:

FIG. 4 is an illustration of the surgical appliance shown in FIG. 1 as attached to a kneecap.

Figure 1:
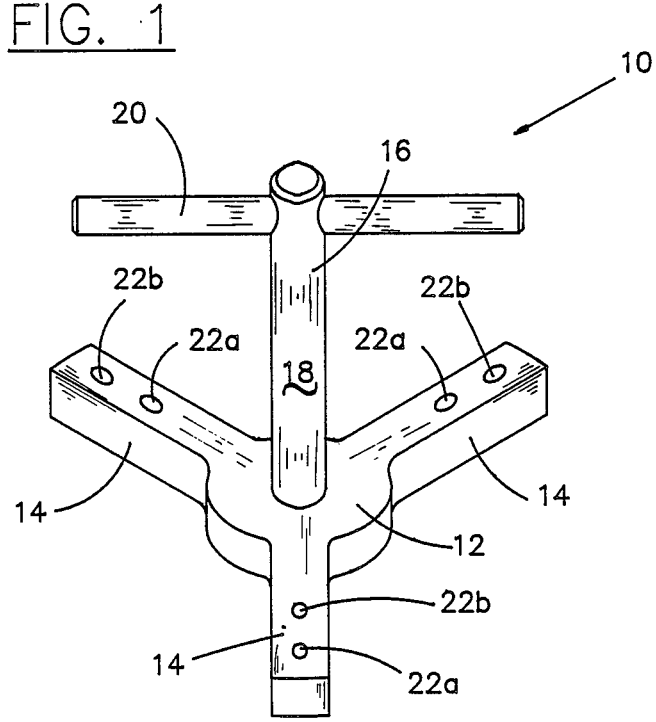
FIG. 1 is a perspective view of the surgical appliance of the present invention.
Figure 2:
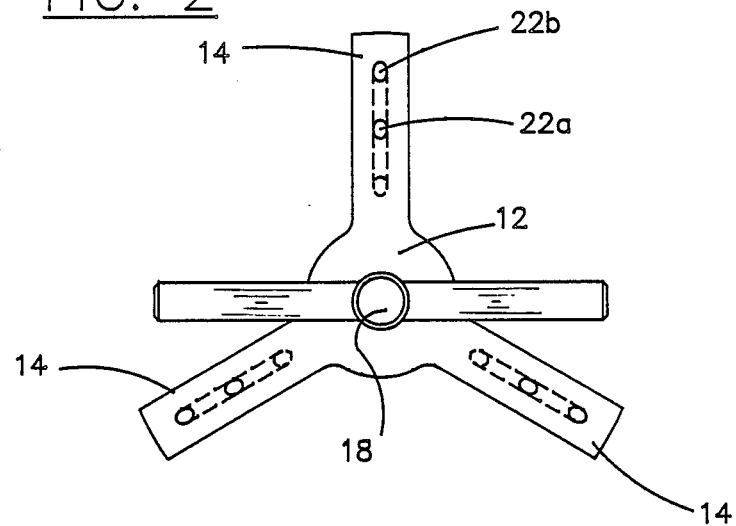
FIG. 2 is a top view of the surgical appliance shown in FIG. 1.
Figure 3:
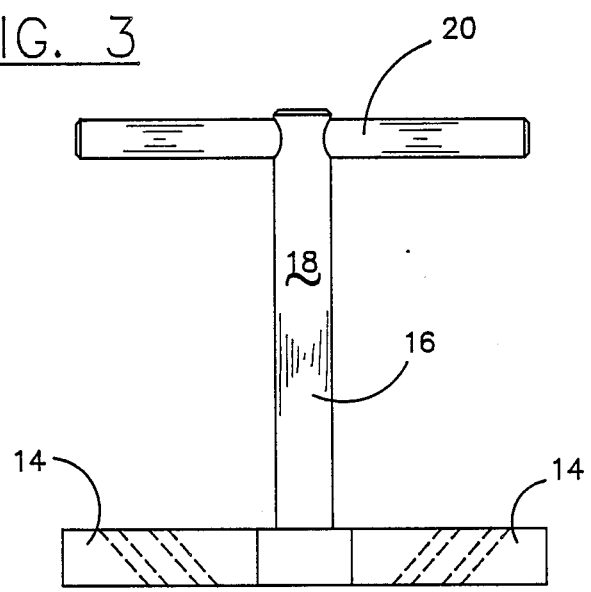
FIG. 3 is a side elevation view of the surgical appliance shown in FIG. 1.

With reference to FIGS. 1, 2 and 3, the surgical appliance of the present invention is generally indicated at 10. As shown, the appliance 10 is comprised of a base portion 12 which is preferably circular in shape having a plurality of arms 14 extending radially outwardly therefrom in the same plane thereof and grasping means 16 affixed to said base portion 12 along the vertical axis thereof. Said grasping means is further comprised of a vertical portion or shaft 18 and a horizontal portion 20 disposed adjacent the upper end and perpendicular to said vertical portion 18 so as to form a "T" shaped handle.

As best seen in FIGS. 1 and 2, the arms 14 are positioned equi-angularly about the periphery of said base portion 12. In the preferred embodiment shown, there are three arms 14 each being spaced approximately 120° apart around said base portion 12. As is further depicted, each arm 14 is provided with a plurality of guide holes 22. The first of said holes 22a on each arm 14 are located on a first circle of centers and the second of said holes 22b on each arm 14 are located on a second circle of centers. As shown in FIG. 2, said first holes 22a are equi-distant from the center of the base portion 12 and said second holes 22b are also equi-distant from the center of said base portion 12.

The holes 22, which are drilled through each arm 14, are positioned and disposed therein at an angle "a" relative to the vertical axis of the base portion 12 and grasping means 16. Said angle "a" may be from about 15° to about 75°, preferably 45°. Said guide holes are dimensioned to receive a small pin or K-wire as will be explained below.

In using the appliance of the present invention, the device is positioned against the patella 24 (see FIG. 4) and pins 26 are inserted into each of the guide holes 22 of one circle of centers and driven through the skin into the patella 24. Once the pins 26 are in place, the appliance 10 is locked into a set position relative to the patella 24 and can neither be advanced towards nor pulled away therefrom. This locking feature is afforded by the relationship between the pins 26 in the angled guide holes 22 of the device relative to the patella. Once the pins are in place, the surgeon or his assistant can shift or move the patella in any direction by merely grasping the "T" shaped handle 16 of the device 10 and moving same. The movement control afforded by the use of the device of the present invention allows a surgeon to achieve optimal visualization of the undersurface of the patella with an arthroscope respecting, of course, the limitation of the soft tissue attachments of the patella.

From the above description, it should be clear to those skilled in the art that the orthopaedic appliance disclosed herein provides a means for positive manipulation of the patella without the use of bone screws, bolts or other tightening means. It is simple in structure and in use.

Furthermore, while the present invention has been described in particularly with reference to the drawings, it will be readily understood by those skilled in the art that further modification and change may be made thereto without departing from the spirit or scope of the invention.

What is claimed is:

1. An orthopaedic appliance for use in manipulating a patella during arthroscopic surgery, said appliance comprising
    a base portion,
    a plurality of arms extending radially outwardly from said base portion in the same plane thereof,
    grasping means affixed to the center of said base portion and extending upwardly perpendicular thereto,
    at least one guide hole located in each of said arms said guide holes being equi-distant from the center of said base portion and being disposed in each of said arms at an angle of from about 15° to about 75° relative to the plane of said base portion, and
    pins which are receivable by said guide holes whereby said pins when disposed in said guide holes and driven into the patella lock said appliance to said patella.

2. The orthopaedic appliance of claim 1 wherein said base portion has three arms extending outwardly therefrom, said arms being equi-angularly spaced from one another.

3. The orthopaedic appliance of claim 1 wherein said grasping means comprises a "T" shaped handle affixed to said base portion.

4. The orthopaedic appliance of claim 1 wherein said guide holes are positioned in each of said arms at about a 45° angle.

5. An orthopaedic appliance for use in manipulating a patella during arthroscopic surgery, said appliance comprising a circular base portion, three arms extending radially outwardly from said base portion in the same plane thereof, said arms being equi-angularly spaced from one another, at least one guide hole disposed in each of said arms, said guide holes being equi-distant from the center of said base portion, said guide holes being disposed in said arms at an angle of about 45° relative to the plane of said base portion, grapsing means affixed to the center of said base portion, said grasping means comprising a "T" shaped handle, and, pins received in said guide holes and adapted to be driven into said patella whereby said appliance and patella are locked together.

* * * * *